United States Patent
Benhar et al.

(10) Patent No.: US 9,925,275 B2
(45) Date of Patent: *Mar. 27, 2018

(54) AMPHOTERICIN B DERIVATIVES

(71) Applicants: RAMOT AT TEL-AVIV UNIVERSITY LTD., Tel Aviv (IL); TECHNION RESEARCH & DEVELOPMENT FOUNDATION LTD., Haifa (IL)

(72) Inventors: Itai Benhar, Rehovot (IL); Nir Osherov, Tel Aviv (IL); Vladimir Dergachev, Netanya (IL); Alex Martin Szpilman, Kiryat Tivion (IL)

(73) Assignees: TECHNION RESEARCH & DEVELOPMENT FOUNDATION LTD., Haifa (IL); RAMOT AT TEL-AVIV UNIVERSITY LTD., Tel Aviv (IL)

(*) Notice: Subject to any disclaimer, the term of this patent is extended or adjusted under 35 U.S.C. 154(b) by 0 days.

This patent is subject to a terminal disclaimer.

(21) Appl. No.: 15/657,649

(22) Filed: Jul. 24, 2017

(65) Prior Publication Data
US 2017/0319705 A1  Nov. 9, 2017

Related U.S. Application Data

(66) Continuation of application No. 15/236,875, filed on Aug. 15, 2016, now Pat. No. 9,750,817, Substitute for application No. 62/204,502, filed on Aug. 13, 2015.

(51) Int. Cl.
| | |
|---|---|
| *A61K 31/7048* | (2006.01) |
| *A61K 47/60* | (2017.01) |
| *C08G 65/333* | (2006.01) |
| *C08G 65/332* | (2006.01) |
| *C08G 65/331* | (2006.01) |
| *C08G 65/329* | (2006.01) |
| *C08G 65/08* | (2006.01) |
| *C07H 17/08* | (2006.01) |

(52) U.S. Cl.
CPC .......... *A61K 47/60* (2017.08); *A61K 31/7048* (2013.01); *C07H 17/08* (2013.01); *C08G 65/08* (2013.01); *C08G 65/329* (2013.01); *C08G 65/333* (2013.01); *C08G 65/3312* (2013.01); *C08G 65/3314* (2013.01); *C08G 65/3322* (2013.01)

(58) Field of Classification Search
None
See application file for complete search history.

(56) References Cited

U.S. PATENT DOCUMENTS

2002/0210527  9/2006  Davis

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*
Wolff, Manfred E. "Burger's Medicinal Chemistry, 5ed, Part 1", John Wiley & Sons, 1995, pp. 975-977.

* cited by examiner

*Primary Examiner* — Traviss C McIntosh, III
(74) *Attorney, Agent, or Firm* — Browdy and Neimark, PLLC

(57) ABSTRACT

Embodiments of the invention provide derivatives of Amphotericin B having increased solubility and reduced toxicity relative to AMB, while retaining antifungal activity against multiple clinical fungal isolates. Derivatives of AMB are provided comprising a polymer group having an amine group, the polymer linked to mycosamine via a relatively stable linker such as an amide linker. The derivatives may be of the general formula [I]:

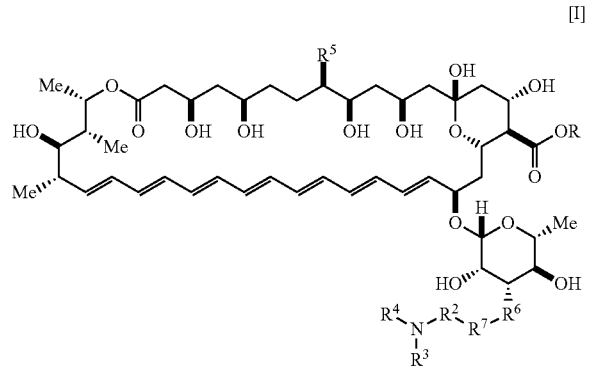

wherein R is H, $C_{1-4}$ alkyl or phenyl; $R^2$ is $(CH_2)_m$ wherein m is between 0 and 4; $R^3$ and $R^4$ are each independently H or $C_{1-4}$ alkyl, $R^5$ is or OH, $R^6$ is selected from a group consisting of: amide and alkyl, and $R^7$ is a water-soluble polymer, and pharmaceutically acceptable salts, solvates, hydrates, diastereomers, and prodrugs of the compound of Formula [I].

12 Claims, 8 Drawing Sheets

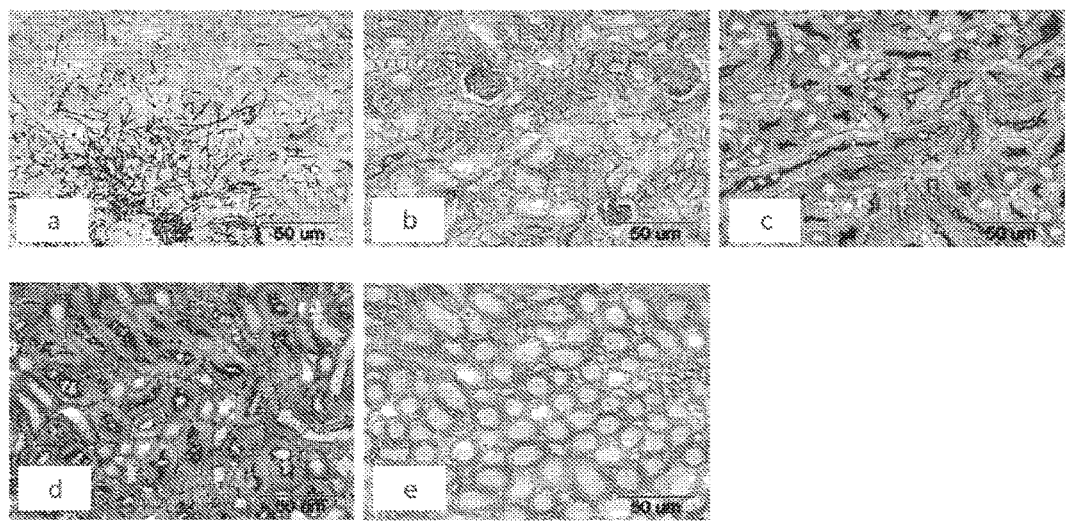
Fig. 6A-E
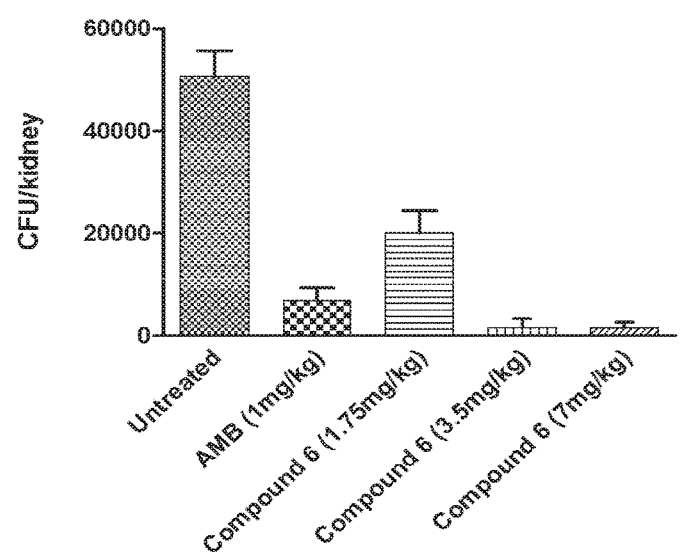
Fig. 7A

AMPHOTERICIN B DERIVATIVES

RELATED APPLICATIONS

The present application claims the benefit under 35 U.S.C. 119(e) of U.S. Provisional Application 62/204,502, filed on Aug. 13, 2015, the disclosure of which is incorporated herein by reference.

TECHNICAL FIELD

Embodiments of the invention relate to novel derivatives of Amphotericin B and methods of treatment associated with the derivatives.

BACKGROUND

Systemic fungal infections are a prevalent health problem impacting immunocompromised patients such as organ transplanted patients and patients treated with chemotherapy. Several known fungicidal agents are currently in use for treating fungal infections. One class of such agents is "polyenes" which act to kill fungal cells by targeting the fungal cell membrane. Amphotericin B (AMB), a polyene macrolide antibiotic first isolated from the soil bacterium *Streptormyces nodosus*, has been used for the last 60 years as a "gold standard" antifungal drug for the treatment of a wide array of systemic mycotic infections and parasitic-derived leishmanial disease. Amphotericin B has also been successfully used in treating Leishmaniasis, a parasitic disease caused by protozoa. However, AMB has been associated with a variety of potentially harmful side effects including but not limited to nephrotoxicity. Due to the often dose-limiting toxicity of this natural product, mortality rates for systemic fungal infections persist near 50%.

In addition, AMB has poor solubility in water, and thus attempts have been made to formulate AMB using a variety of technologies such as liposomes and water soluble colloidal complexes.

SUMMARY

Embodiments of the invention provide derivatives of Amphotericin B having increased solubility and reduced toxicity relative to AMB, while retaining antifungal activity against multiple clinical fungal isolates.

A derivative according to an embodiment of the invention comprises a water-soluble polymer such as a polyethylene glycol (PEG) moiety.

An AMB derivative according to embodiments of the invention may be substituted with an amide group.

An AMB derivative in accordance with an embodiment of the invention, comprising a water soluble polymer group having an amine group, the water soluble polymer group being linked to mycosamine via a relatively stable linker such as an amide linker, may be referred to herein as a Polymer-Amine Derivative of AMB (PAD-AMB). In certain embodiments of the invention, the water soluble polymer group is a PEG group.

PAD-AMB may have an ester, such as an alkyl ester modification of the native AMB carboxyl group. PEG is a polymer of ethylene oxide or derivatives thereof. An individual ethylene oxide or derivative comprised in the PEG moiety may be referred to herein as a "PEG monomer".

PAD-AMD, according to embodiments of the invention may be of the general formula [I]:

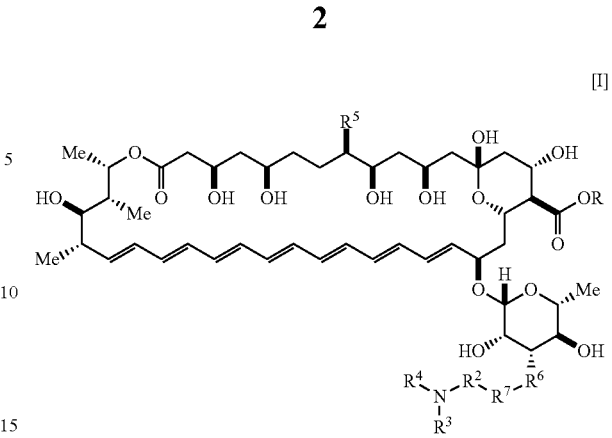

wherein R is H, $C_{1-4}$ alkyl or phenyl; $R^2$ is $(CH_2)_m$ wherein m is between 0 and 4; $R^3$ and $R^4$ are each independently H or $C_{1-4}$ alkyl, $R^5$ is H or OH, $R^6$ is selected from a group consisting of: amide and alkyl, and $R^7$ is a water-soluble polymer, and pharmaceutically acceptable salts, solvates, hydrates, and stereoisomers thereof, including mixtures thereof in all ratios. Optionally, the amide is selected from a group consisting of: organic amide, sulfonamide, sulfenyl amide and phosphoramide, and pharmaceutically acceptable salts, solvates, hydrates and stereoisomers thereof, including mixtures thereof in all ratios. Optionally, the water-soluble polymer is a PEG group having p PEG monomers wherein p is from 6 to 40, or preferably wherein p is from 6 to 10, or preferably wherein p is 8.

In certain embodiments of the invention, the PAD-AMB may be of the formula [II]:

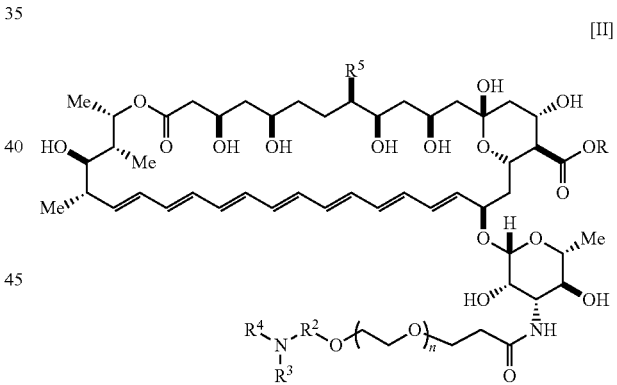

wherein R is H, $C_{1-4}$ alkyl or phenyl; $R^2$ is $(CH_2)_m$ wherein m is between 1 and 4; $R^3$ and $R^4$ are each H or $C_{1-4}$ alkyl, $R^5$ is H or OH and n is between 5 and 39. Optionally, n is between 5 and 9, or n is 7. Optionally, PAD-AMB may be in the form of a pharmaceutically acceptable salt, solvate, hydrate, diastereomer, and/or prodrugs of the compound of general formula I. Optionally, $R^2$ is ethyl ($CH_2$—$CH_2$). Optionally, $R^3$ and $R^4$ are each H. Optionally, $R^5$ is OH. Optionally, n is 7. According to a preferred embodiment of the invention, R is H, $R^2$ is ethyl, $R^3$ and $R^4$ are each H, is OH and n is 7. According to a preferred embodiment of the invention, R is $CH_3$ $R^2$ is ethyl, $R^3$ and $R^4$ are each H, $R^5$ is OH and n is 7.

In addition to novel derivatives, embodiments of the invention provide methods of treatment of disease using PAD-AMB. Diseases which may be treated using PAD-AMB include parasitic and fungal diseases. Exemplary diseases include systemic fungal infection and protozoan disease such as leishmaniasis. Additional diseases which may be treated using PAD-AMB may include viral and prion diseases. According to an embodiment of the invention, PAD-AMB derivatives are useful in immunocompromised patients.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF FIGURES

FIGS. 6A-E show micrographs of kidney sections from mice challenged with fungal infection and not treated (6A) or treated with AMB at 1 mg/kg (6B) or Compound 6 at 1.75, 3.5 and 7 mg/kg (6C-E respectively);

FIGS. 7A-B show a graph showing colony-forming units (CFU) per kidney (7A) or per spleen (7B) of mouse after fungal infection and subsequent treatment with AMB or various doses of Compound 6.

DETAILED DESCRIPTION

Figure 1A:
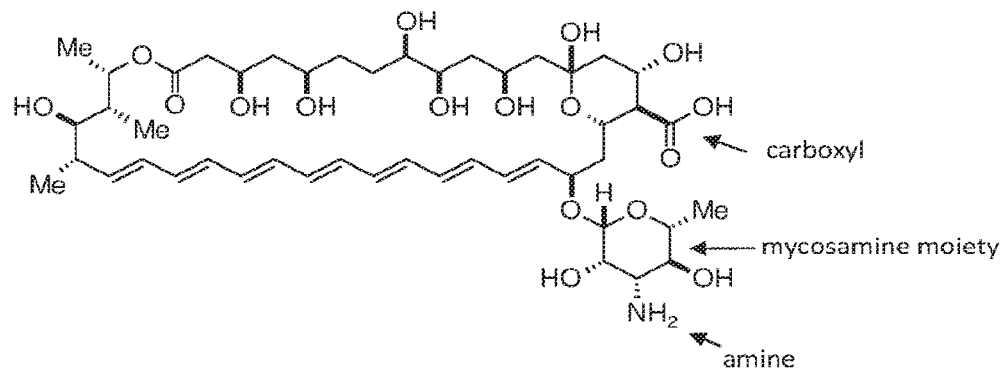
FIG. 1A depicts the structural formula of amphotericin B.

FIG. 1A shows the structure of Amphotericin B. As can be seen in the figure, Amphotericin B comprises a mycosamine moiety having an amine group. Previous attempts have been made to conjugate a PEG to the amine group of the mycosamine of AMB using a carbamate linker. The carbamate bond is susceptible to enzymatic hydrolysis in vivo which is believed to result in cleavage of the AMB moiety from the PEG moiety. While these derivatives having a hydrolyzable linker exhibited improved water-solubility, they also had similar toxicity shortcomings characteristic of the parent AMB.

Figure 1B:
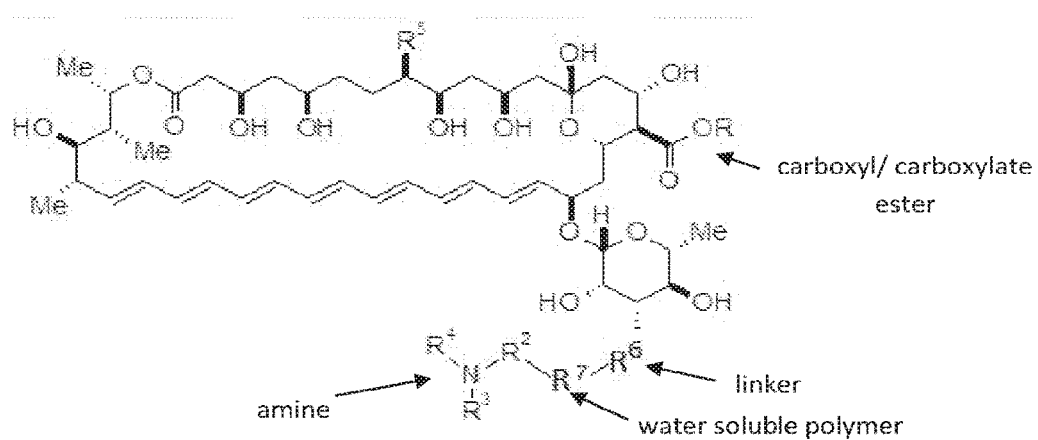
FIG. 1B depicts a general structural formula of PAD-AMB according to embodiments of the invention.
Figure 1C:
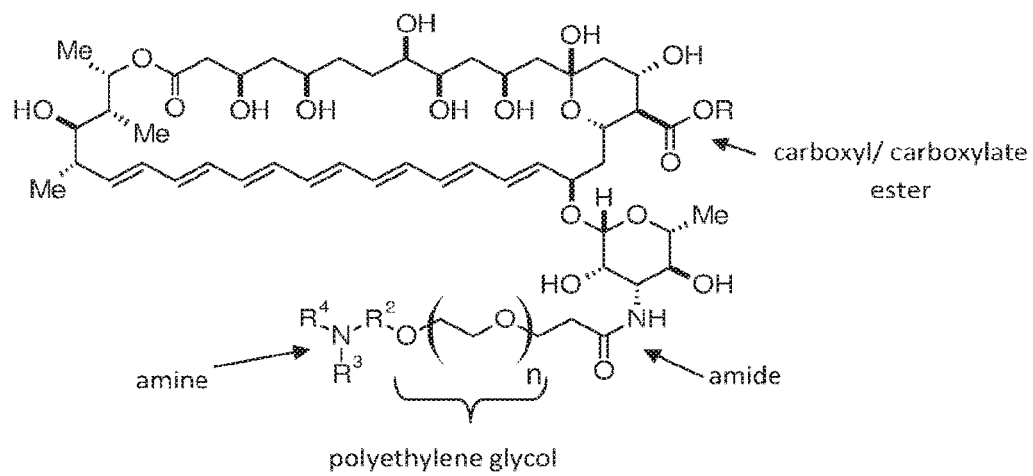
FIG. 1C depicts a general structural formula of PAD-AMB comprising PEG according to embodiments of the invention.

FIG. 1B shows a PAD-AMB in accordance with embodiments of the invention, in which a water soluble polymer amine group is linked to the Amphotericin B amine of the mycosamine with a linker that is not susceptible to rapid enzymatic hydrolysis. FIG. 1C, shows a PAD-AMD in accordance with embodiments of the invention in which polyethylene glycol (PEG) is linked to the Amphotericin B amine of the mycosamine through an amide bond, which is not susceptible to rapid enzymatic hydrolysis. Without being bound by theory, it is suggested that PAD-AMB according to embodiments of the invention do not undergo enzymatic hydrolysis as the amide group is not susceptible to hydrolysis.

Alternate linkers other than or in addition to an amide linker may be used to conjugate water soluble polymer amine groups, by way of example PEG amine groups, to the mycosamine of Amphotericin B according to embodiments of the invention. Such linkers do not undergo hydrolysis or cleavage easily in vivo. For example, such linkers may not undergo detectable hydrolysis in up to 4 hours in serum-like media conditions. Exemplary linkers which may be used according to embodiments of the invention include sulfonamide, sulfenyl amide and phosphoramide. Alternatively, an alkyl linker may be used. The alkyl linker may be linked by reductive amination with an aldehyde functionality on the PEG chain.

PAD-AMB according to embodiments of the invention may comprise polymer chains of various lengths, preferably between 6 and 40 monomers. In a preferred embodiments of the invention, the polymer group in a PAD-AMB molecule comprises between 6 and 10 monomers, most preferably 8 monomers. PAD-AMB according to embodiments of the invention may comprise 6, 7, 8, 9, 10, 11 . . . 40 monomers according to embodiments of the invention. One of the monomers may be an ethanolamine group, having a primary amine at its terminus.

In an embodiment of the invention, the polymer may be a PEG. PAD-AMB comprising PEG according to embodiments of the invention may comprise PEG chains of various lengths, preferably between 6 and 40 PEG monomers (ethylene oxide monomers). In a preferred embodiments of the invention, the PEG group in a PAD-AMB molecule comprises between 6 and 10, monomers, most preferably 8 PEG monomers. PAD-AMB according to embodiments of the invention may comprise 6, 7, 8, 9, 10, 11 . . . 40 PEG monomers according to embodiments of the invention. One of the PEG monomers may be an ethanolamine group, having a primary amine at its terminus.

PAD-AMB may comprise a carboxyl group or a carboxylate, ester group. Methyl ester, ethyl ester, propyl ester and phenyl ester may be used according to various embodiments of the invention.

Without being bound by theory, it is suggested that PAD-AMB is active in vivo in its water soluble polymer-containing form. PAD-AMB molecules are not easily cleaved in vivo and have anti-fungal and anti-protozoan effect in their water-soluble polymer-containing form. It is suggested that the primary amine of the polymer-amine group contributes to the PAD-AMB molecule's antifungal and anti-protozoan effect. This was confirmed by determination of the minimal inhibitory concentration of PAD-AMB comprising PEG as the polymer in which the primary amine was "protected" on the fungi Aspergillus fumigatus and C. albicans.

The most clinically important invasive opportunistic fungal pathogens belong to one of the four groups: *Aspergillus, Candida, Cryptococcus* and *Pneumocystis*. They are responsible for the majority of morbidity and 90% of lethal fungal-related cases. According to an embodiment of the invention, the fungal pathogen that may be treated using PAD-AMB is selected from the group consisting of: *Aspergillus, Candida, Cryptococcus* and *Pneumocystis.*

PAD-AMB may be in the form of a pharmaceutically acceptable salt. The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound. The neutral forms of the compounds are preferably regenerated by contacting the salt with a base or acid and isolating the parent compound in a conventional manner. The parent form of the compound differs from the various salt forms in certain physical properties, such as solubility in polar solvents, but otherwise the salts may be essentially equivalent to the parent form of the compound for the purposes of the present invention.

PAD-AMB may be provided in a pharmaceutical composition via oral administration. PAD-AMB may be provided in a pharmaceutical composition via injection, for example intravenous, subcutaneous or intramuscular injection. PAD-AMB may be provided in a pharmaceutical composition via topical administration.

The pharmaceutical compositions according to an embodiment of the invention may be conveniently presented in unit dosage form and may be prepared by any of methods well known in the art of pharmacy. In an embodiment of the invention, the unit dosage form is in the form of a vial, pre-filled syringe, tablet, capsule, lozenge, wafer, powder or liquid form. The compositions of the present invention are generally administered in the form of a pharmaceutical composition comprising at least one active component together with a pharmaceutically acceptable carrier or diluent.

According to an embodiment of the invention, an aqueous pharmaceutical composition is provided. According to an embodiment of the invention, the aqueous pharmaceutical composition comprises at least 50% water.

For oral administration, a pharmaceutical composition can take the form of solutions, suspensions, tablets, pills, capsules, powders, and the like. Tablets containing various excipients such as sodium citrate, calcium carbonate and calcium phosphate are employed along with various disintegrants.

The compositions according to embodiments of this invention may also be administered in a controlled release formulation such as a slow release or a fast release formulation. Such controlled release dosage composition may be prepared using methods known to those skilled in the art.

Pharmaceutical compositions according to embodiments of the invention may contain an active amount of 0.1%-95% (by weight basis relative to total composition) of the PAD-AMB, preferably 1%-70%.

Methods of treatment of disease may comprise administering to a patient in need thereof a therapeutically effective amount of a PAD-AMB. According to an embodiment of the invention, an amount of between 0.5 milligrams per kilogram body weight (mg/kg) and 4.0 mg/kg is administered to the patient in need thereof. According to an embodiment of the invention, a therapeutically effective amount of PAD-AMB is administered once daily. According to an embodiment of the invention, an amount of up to 10 mg/kg is administered to the patient in need thereof.

Figure 2:
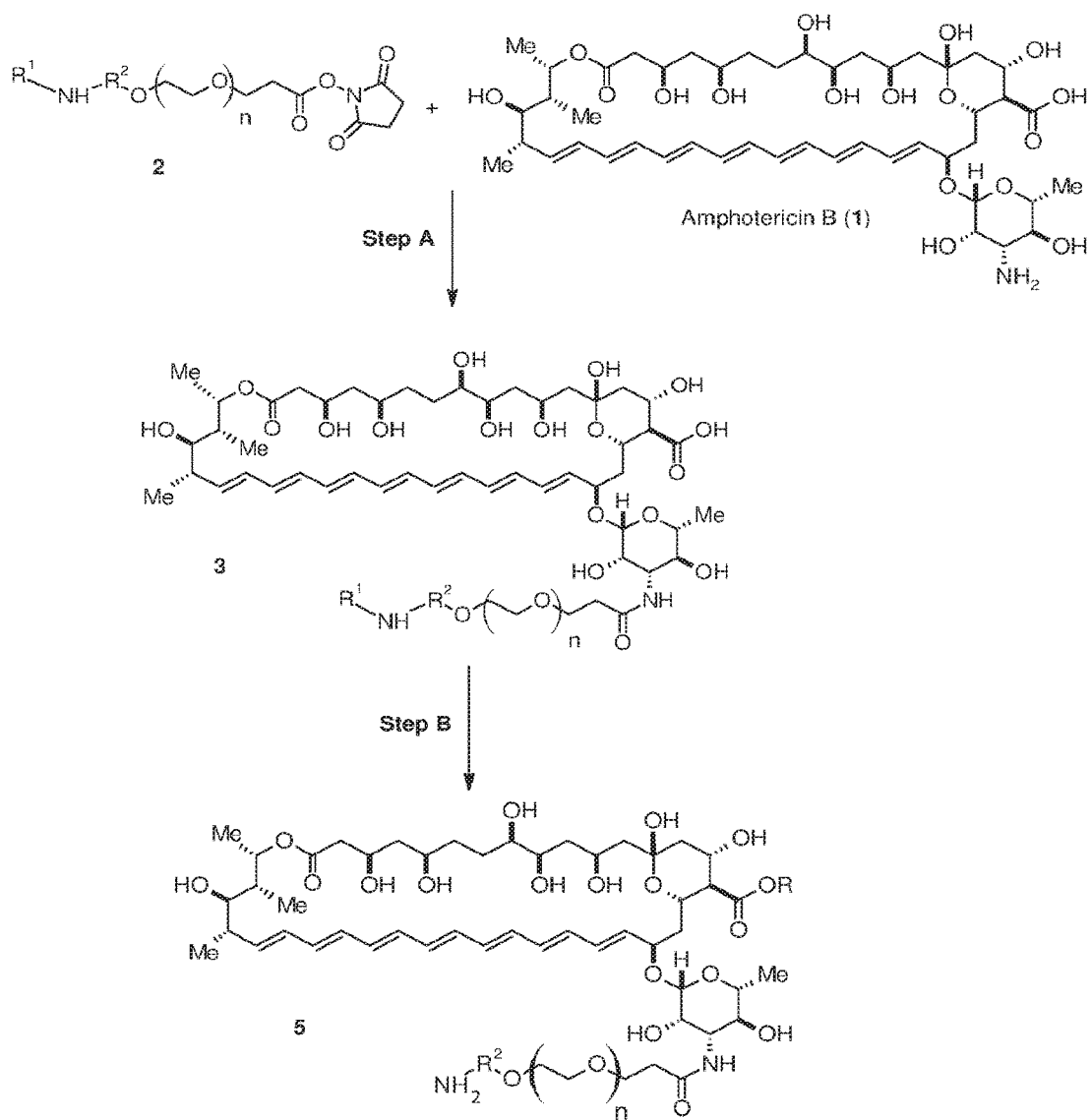
FIG. 2 depicts a general method of manufacture of PAD-AMB according to embodiments of the invention from an amphotericin B starting material.

Reference is now made to FIG. 2 which depicts a general method of manufacture of PAD-AMB according to embodiments of the invention. PAD-AMB may be manufactured in a two-step process comprising Step A and Step B as shown in FIG. 2.

Step A comprises reacting amphotericin B (designated as compound 1) with a protected amine N-hydroxysuccinimide ester of PEG as depicted by compound 2, in which $R^1$ is a protecting group. The protecting group $R^1$ may be a fluorenylmethyloxycarbonyl (FMOC) group. Other protecting groups which may be used include azide groups, 2,-nitrophenyl-sulfonyl, and 4-nitro-phenyl-sulfonyl, and 2,4-dinitrophenylsulfonyl. The integer n may represent between 5 and 39 PEG monomers, preferably between 5 and 9, preferably 7. The reaction may be performed in a non-aqueous solvent such as dimethylformamide (DMF). The reaction may be performed in the presence of a tertiary amine. The tertiary amine may be pyridine. The reaction may be performed under an inert atmosphere. The reaction may be performed in a light-free environment. The reaction mixture may be stirred for about 24 hours (h). The product, compound 3, may be isolated, for example using a chromatographic column.

Step, B for removal of the protecting group $R^1$, may be performed through hydrolysis. The hydrolysis may be performed by contacting compound 3 with a weak base. The weak base may be an amine, preferably a secondary amine. The secondary amine may be piperidine. The hydrolysis may be performed in a non-aqueous solvent. The non-aqueous solvent may be DMF. The resulting product is a compound of general formula 5.

Alternatively or additionally, before performing Step B, the Amphotericin B carboxyl group may be transformed into a carboxylate ester. A methylating agent may be added, for example, to transform compound 3 to a methyl ester. For example, the methylating agent (trimethylsilyl)diazomethane in the presence of methanol may be added in excess to compound B. Other methylating agents may include dimethylsulfate and methyliodide in the presence of a base such as $K_2CO_3$. The carboxylic ester product may then proceed to Step B for removal of the protecting group.

Alternatively, instead of using AMB as a starting compound, 8-deoxyamphotericins may be used as starting material. The process as described above may be followed with 8-deoxyamphotericins to obtain compound of general formula [II] wherein $R^5$ is H. The compound 8-deoxyamphotericin may be obtained by synthesis as described previously in Byrne et al. (Chem Biol. 2003 December; 10(12):1215-24.)

Example 1, Manufacture of Compound 4

Figure 3A:
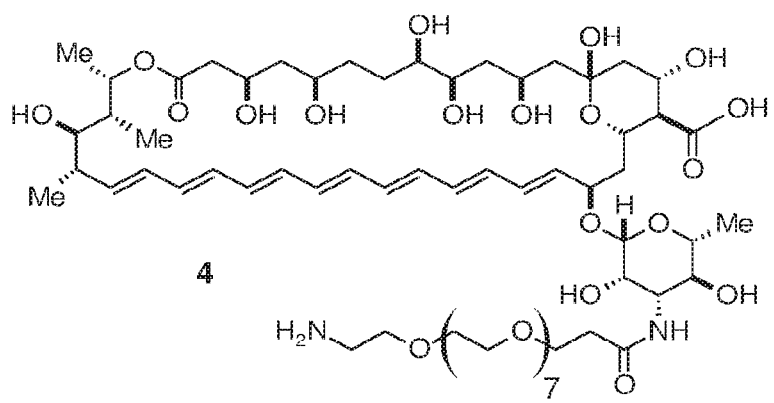
FIGS. 3A-B depict structural formulae of PAD-AMB compounds 4 and 6 respectively according to embodiments of the invention.

FIG. 3A depicts compound 4, a PAD-AMB according to embodiments of the invention. Compound 4 is amphotericin B amide-PEG(8)-amine. Compound 4 was synthesized as follows:

Amphotericin B (50 mg, 1 equivalent, available from Appollo Scientific, UK) was reacted with FMOC-protected N-hydroxysuccinimide ester of PEG having 8 PEG monomers (compound 2 of FIG. 2 wherein n is 7, $R^1$ is FMOC, $R^2$ is ethyl and $R^3$ is H, 49.5 mg, 1.2 equivalents, available from Iris Biotech GmbH, Germany) in 2 milliliters (ml) dry DMF in the presence of pyridine (1.2 equivalents) while stirring under inert atmosphere (argon) and exclusion of light for 23 h. The reaction mixture was poured into excess cold diethyl ether, washed twice with ether and dried under vacuum. The product was purified on a silica gel column (CHCl$_3$/MeOH/H$_2$O 10:4:0.3, Rf=0.64) to give a corresponding FMOC-protected amine derivative as a pale yellow powder (40 mg, 47% yield). The FMOC group was then removed using 3 ml of 30% piperidine in DMF for 30 minutes at room temperature. The final product was recovered by precipitation with cold diethyl ether, washed twice and centrifuged (CHCl$_3$/MeOH/H$_2$O 10:4:0.3, Rf=0.5). The obtained yellow product (Compound 4) (28 mg, 82% yield) was lyophilized and stored at −20° C. under argon in the dark until further use. The resulting product was confirmed to be compound 4 using NMR, IR thin film and HRMS.

Example 2, Manufacture of Compound 6

Figure 3B:
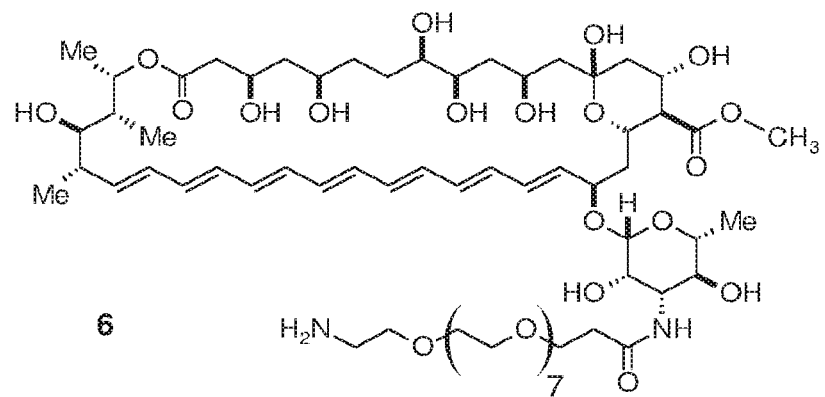

FIG. 3B depicts compound 6, a PAD-AMB according to embodiments of the invention. Compound 6 is amphotericin B amide, methyl ester-PEG(8)-amine, having 8 PEG monomers. Compound 6 was synthesized as follows: FMOC-protected amine derivative of compound 4 was prepared as described in Example 1. 50 mg, 1 equivalent of the FMOC-protected amine was dissolved in 2 ml dry DMF, cooled on ice and (trimethylsilyl)diazomethane solution (4 equivalents, 2.0 M in hexanes) was added and brought to room temperature, followed by stirring for 3 h. The reaction mixture was poured into excess cold diethyl ether, washed twice with ether and dried under vacuum. The product was purified on a silica gel column (CHCl$_3$/MeOH/H$_2$O 10:1.7:0.05, Rf=0.43) to give the methyl ester of the FMOC-protected amine as a pale yellow powder (13.61 mg, 27% yield). The FMOC group was removed as described in Example 1. The final product was purified by flash chromatography (CHCl$_3$/MeOH/H$_2$O 10:4:0.3, Rf=0.59) to give an orange powder (4.16 mg, 36% yield). The resulting product was confirmed to be compound 6 using NMR, IR thin film and HRMS.

Example 3—Manufacture of Derivatives of AMB Comprising p PEG Monomers (PEG(p)), an Amine Group and an Amide Linker Compounds were manufactured having different numbers of PEG monomers, using the synthetic procedures described in example 1 (for carboxylic acid compounds) and in example 2 (for methyl ester compounds) using the FMOC-protected N-hydroxysuccinimide ester having the appropriate number of PEG monomers. The molecular weight and shorthand name of the compounds, and their structure according to general formula [II] are listed in Table 1 below, in which "AMB" is shorthand for Amphotericin B and "AME" is shorthand for Amphotericin methyl ester:

TABLE 1

| Name | p | R | Molecular weight |
|---|---|---|---|
| AMB-PEG4-amine | 3 | H | 1171 |
| AME-PEG4-amine | 3 | CH$_3$ | 1185 |
| AMB-PEG44-amine | 43 | H | 2602 |
| AME-PEG44-amine | 43 | CH$_3$ | 2616 |

Example 4a: Physical Characteristics of AMB Derivatives: Solubility

Physical characteristics of AMB derivatives and of AMB were tested, including solubility. The solubility of PAD-AMB derivatives according to embodiments of the invention in double-distilled water is detailed below in Table 2 relative to other compounds, including AMB and its corresponding methyl ester.

TABLE 2

| Compound | Solubility (mg/ml) |
|---|---|
| Amphotericin B | <0.001 |
| Amphotericin B methyl ester | <0.001 |
| AMB-PEG4-amine | 0.3 |
| AME-PEG4-amine | Insoluble |
| Compound 4 | 5.5 |
| Compound 6 | 0.7 |
| AMB-PEG44-amine | Not tested |
| AME-PEG44-amine | 10 |

As shown in Table 2, AMB and its corresponding methyl ester are each essentially insoluble in water, as is AME-PEG4-amine. AMB-PEG4-amine showed low water solubility. Compound 6 and especially compound 4 showed improved solubility. When tested in 0.9% saline after vortex (5 minutes), sonication (2 minutes) and centrifuge (10 minutes at 14,000 revolutions per minute, RPM), compounds 4 and 6 showed increased solubility (greater than 5500-fold and greater than 700 fold respectively) relative to corresponding non-PEG-conjugated AMB compounds, making them easy to formulate and administer via aqueous solutions.

While water solubility improves with increasing length of the PEG conjugate, the potency is generally decreased. A value of PEG-chain p between 6 and 10 appears to provide a good balance between the two opposing trends.

Example 4b: Physical Characteristics of AMB Derivatives: Stability

Compounds 4 and 6 were stable in phosphate buffered saline, and no hydrolysis could be observed after 4 hours in the buffer. More prolonged incubation for 24 hours resulted in a low level of hydrolysis of 0.51% and 0.8% for compounds 4 and 6 respectively.

Example 5a: In-Vitro Study of Efficacy of PAD-AMB Against Clinical Isolates

Isolates of *Aspergillus* fumigatus, *Aspergillus* flavus, *Aspergillus* terreus *Aspergillus* niger, *Rhizopus* oryzae, *Candida* albicans and *Candida* krusei were isolated from patients in Israeli hospitals and used for in vitro efficacy studies.

Efficacy was evaluated by measuring minimum inhibitory concentration (MIC) and minimum fungicidal concentration (MFC) values for fungal isolates. Testing of isolates was performed according to the Clinical & Laboratory Standards Institute (CLSI) method. (CLSI. 2008. M27-A3 Reference method for broth dilution antifungal susceptibility testing of yeasts; Approved Standard—3rd edition. Clinical and Laboratory Standards Institute, Wayne). RPMI MOPS media was used throughout the experiment as growth and dilution media. Spores and yeast cells were harvested in 0.05% Tween from 24-48 h and cultures were grown in rich yeast extract-agar-glucose (YAG) medium (composed of: 0.5% w/v yeast extract, 1% w/v glucose, 10 millimolar (mM) MgCl$_2$, supplemented with 0.1% v/v trace elements solution, and 0.2% v/v vitamin mix). The spores and the yeast cells were counted and diluted to a final concentration of $2.5 \times 10^4$ per ml. A stock solution of 5 mg/ml was prepared in dimethylsulfoxide for free AMB. Compounds 4 and 6 were prepared in sterile saline. Double dilutions of each drug were performed in 100 µL volume of RPMI-MOPS in 96 well plates beginning with a final concentration of 32 micrograms (µg)/well of each drug to 0.06 µg/well. 2500 spores or yeast cells were added to each well. Results were recorded 48 h post incubation at 37° C. The MIC was defined as the lowest drug concentration that resulted in complete inhibition of visible growth. The MFC was defined as the lowest drug concentration that yielded three or fewer colonies (i.e. 99% of the inoculum was killed).

MIC and MFC of Compounds 4, 6 and AMB against a variety of isolates is shown in table 3.

medium and grown to an optical density at 600 nanometers ($OD_{600\ nm}$) of 0.5-0.6. Then, cells were counted and diluted to $10^6$ cells/ml in YPD. Compound 6 and amphotericin B (AMB) were added at concentrations 2-fold above the MIC determined for this strain (2 and 0.5 µg/ml, respectively) and shaken at 30° C. At different time points (0, 15 min, 30 min, 1 h, 2 h) samples were removed, diluted and plated on YPD agar (2% agar) plates. Colonies were counted after incubation for 24 h at 30° C. Control measurements included untreated *C. albicans* cells and cells treated with AMB. All time-kill curve studies were conducted in duplicate and in three independent experiments.

TABLE 3

| Strain | Number of Isolates | Comp. 4 MIC µg/ml | Comp. 4 MFC µg/ml | Comp. 6 MIC µg/ml | Comp. 6 MFC µg/ml | AMB MIC µg/ml | AMB MFC µg/ml |
|---|---|---|---|---|---|---|---|
| C. albicans | 2 | 1-2 | 4 | 1 | 2 | 0.25 | 0.5 |
| C. krusei | 3 | 4-8 | 8 | 2 | 4 | 0.5 | 1-2 |
| A. fumigatus | 4 | 4-16 | 4-16 | 1-8 | 2-8 | 0.25-1 | 0.5-4 |
| A. niger | 3 | 1-4 | 1-4 | 2 | 2 | 0.5-1 | 0.5-1 |
| A. Flavus | 3 | 4-8 | 4-8 | 2-4 | 2-4 | 0.5-1 | 0.5-1 |
| C. terreus | 1 | 32 | 32 | 16 | 16 | 2 | 4 |
| Rhizopus | 1 | 8 | 8 | 4 | 4 | 0.25 | 0.25 |

As seen in Table 3, Compounds 4 and 6 were active against a broad range of fungi.

Compound AME-PEG44-amine, synthesized in Example 3, was found to have an MIC of >32 µg/ml against *A. fumigatus*, showing no antifungal activity at the highest concentration that could be tested.

In addition, the amine protected equivalent of compound 6 in which the amine of compound 6 was protected with an FMOC group was tested (designated FMOC-6) to determine MIC versus AMB and versus compound 6 against *A. fumigatus* (Af 293) and *C. albicans* (CBS562). The results of the MIC analysis are tabulated in Table 4 below:

TABLE 4

| Strain | Compound 6 (µg/ml) | AMB (µg/ml) | FMOC-6 (µg/ml) |
|---|---|---|---|
| A. fumigatus | 2 | 0.5 | >32 |
| C. Albicans | 2 | 0.25 | >32 |

The results shown in table 4 indicate that the amine functionality of PAD-AMB and in particular, of compound 6, contributes to their therapeutic and antifungal activity.

With regard to the compound having 4 PEG monomers and addressed above in examples 3 and 4a, their MIC was determined using the aforementioned method. The MIC was determined for AMB-PEG4-amine against *A. fumigatus* was determined to be 2-3 (µg/ml), indicating that the compound is active even though its solubility is significantly lower than the corresponding compound 4, having 8 PEG monomers.

Example 5b: In-Vitro Time-Kill Study of PAD-AMB

Figure 4A:
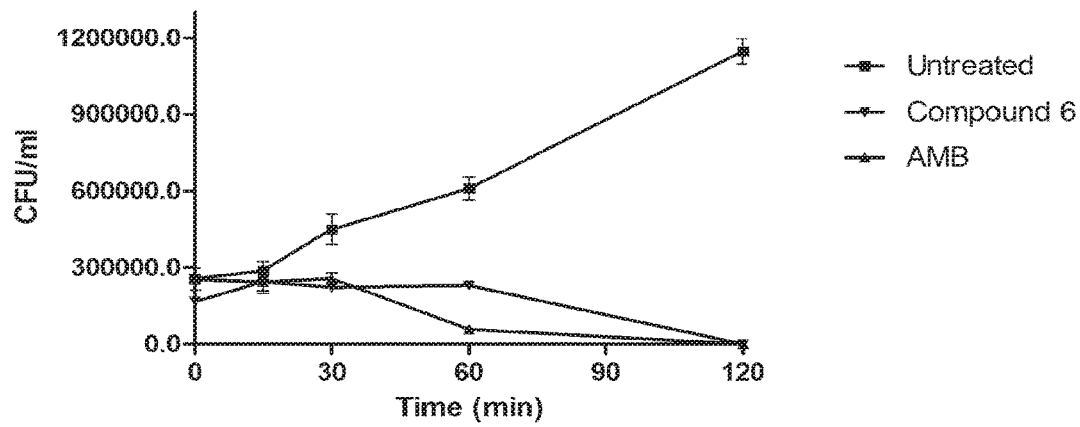
FIG. 4A depicts a time-kill curve showing presence of Candida albicans (C. albicans) in the presence of compound 6, AMB, and no active antifungal agent (untreated) over the course of 2 hours.

In time-kill studies, *C. albicans* CBS 562 was grown overnight from a single colony in 50 ml of liquid YPD medium (composed of 1% (w/v) yeast extract, Difco, 2% w/v peptone, Difco, and 2% w/v dextrose, Merck) at 30° C. On the next day, the starter was diluted 1:100 in the same As shown in FIG. 4A, compound 6 and AMB showed similar activity in the assay, reducing the fungal presence over the course of 2 hours, showing potential use of PAD-AMB as an antifungal agent.

Example 5c: In-Vitro Toxicity (Hermolysis) Study of PAD-AMB in Human Erythrocytes Reference is made to FIG. 4B. Fresh human erythrocytes were diluted 1:100 in PBS, and incubated in an Eppendorf tube while rotating slowly in the presence of 6 µg/ml of each of compound 4 and compound 6. Amphotericin B was used as positive control. Sterile double distilled water served as a control for 100% hemolysis. After 1, 3, 5 and 21 h, 20 µl of each test tube were removed and diluted in 180 µl PBS. Samples were centrifuged for 10 minutes at 1200 RPM and the optical density of the supernatant was measured at 425 nm.

Figure 4B:
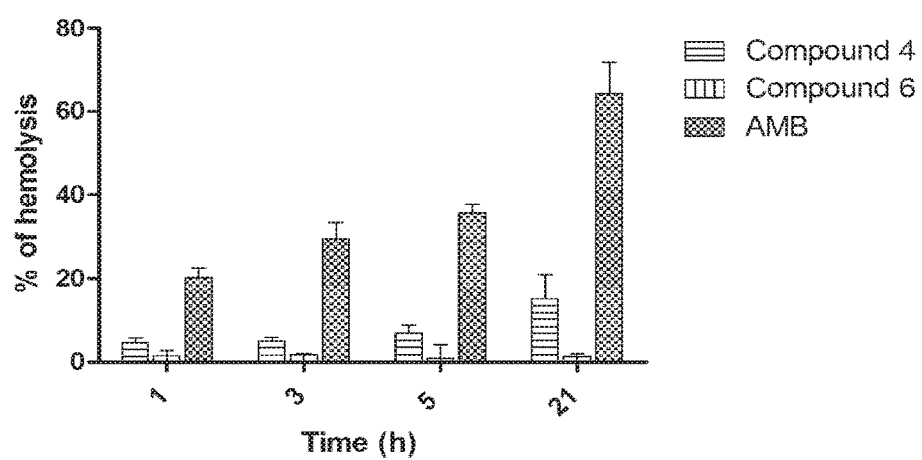
FIG. 4B depicts a histogram showing percent of hemolysis of human red blood cells in the presence of compound 4, 6, or AMB at various time points in a hemolysis assay.

The results of the assay were tabulated as shown in FIG. 4B. The assay showed that compound 4 exhibited small hemolytic activity and compound 6 was only slightly hemolytic at 6 µg/ml after 3 h of agitation, whereas the same concentration of AMB resulted in 76% hemolysis. As shown, AMB is very toxic to erythrocytes, Compound 4 is less toxic (about four times less) and Compound 6 had negligible toxicity under the assay conditions. This shows that PAD-AMB s according to embodiments of the invention may be effective antifungal drugs having more safety than the known antifungal AMB.

Example 5d: In-Vitro Toxicity Study of PAD-AMB in Mouse Embryonic Fibroblasts

Figure 4C:
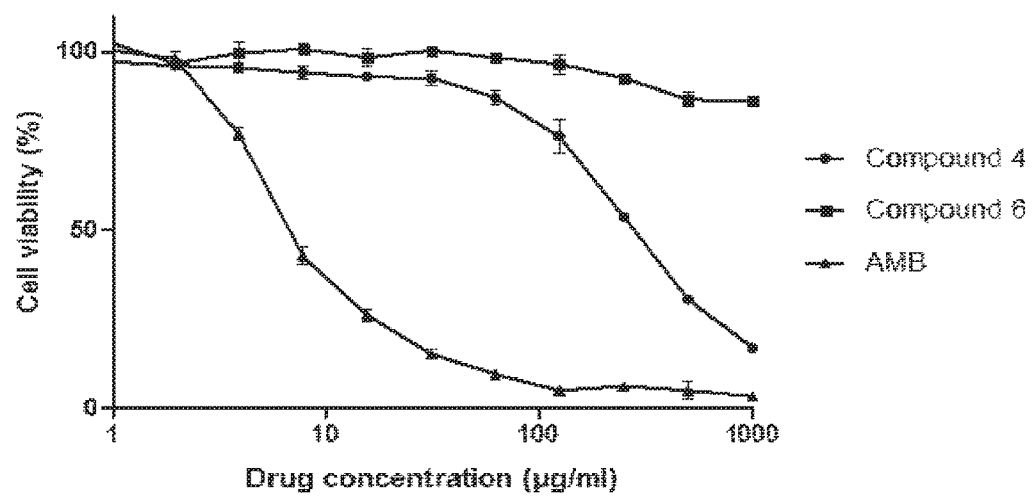
FIG. 4C depicts a histogram showing cell viability of mouse embryonic fibroblasts cells in the presence of various concentrations of compounds 4, 6 and AMB in a viability assay.

Reference is made to FIG. 4C. Mouse embryonic fibroblasts were used in this example. $1 \times 10^4$ mouse embryonic fibroblasts (MEFs) per well were seeded in 96-well plates and incubated at 37° C. After 24 h the media was replaced with 100 µl culture medium containing serial dilutions of AMB, compounds 4 or 6, or left untreated. After 24 h, the media was replaced by fresh media (100 μl per well) containing 1 mg/ml MTT (3-(4,5-Dimethylthiazol-2-yl)-2, 5-Diphenyltetrazolium Bromide. ((Biological Industries, Israel)) reagent and the cells were incubated for an additional 3 h at 37° C. MTT-formazan crystals were dissolved by the addition of 100 μl per well of extraction solution (20% SDS, 50% N,N-dimethyl formamide (DMF), pH=4.7) and incubation for 16 h at 37° C. Absorbance at 570 nm was recorded on a Biotek Synergy HT plate reader.

The results were expressed as the percentage of living cells relative to the untreated control and are depicted in FIG. 4C. The inhibition concentration ($IC_{50}$) value is the concentration of the compound which inhibited cell growth by 50%. AMB had an $IC_{50}$ of 6.6 μg/ml in that assay. Compound 4 had an $IC_{50}$ of 280 μg/ml, 40 times less toxic than AMB. Compound 6 did not affect cell viability at concentrations as high as 1000 mg/ml, suggesting it is at least 600 times less toxic than AMB.

Example 6A: In Vivo Toxicity of PAD-AMB on Mice

In-vivo toxicity was determined in mice using 6 week old female ICR mice (n=6). Different concentrations of each formulation were injected intravenously through the tail vein, 0.2 ml per mouse, until death was observed. PAD-AMB conjugates were prepared in sterile saline solution and were filtered through 0.45-micrometer pore-size cellulose acetate sterile filters prior to injection. In vivo maximum dose reached and $LD_{50}$ dose in mg/kg body weight for each of the tested compounds is shown below in Table 5.

TABLE 5

| Compound | Maximum Dose | $LD_{50}$ |
|---|---|---|
| Compound 4 | 22 | not reached |
| Compound 6 | 42 | not reached |
| AMB | 1.1 | 1.2 |

AMB had an $LD_{50}$ of 1.1 mg/kg, which corresponds to known mouse toxicity values reported for AMB. Compounds 4 and 6 were far less toxic, reaching maximal injected doses of 22 and 42 mg/kg, respectively without any apparent toxicity. The maximal injected doses were determined by the maximal injection volume (200 μl) and solubility in saline of the compounds. For compound 6, the maximal water solubility (0.7 mg/ml) in 200 μl yields 140 μg, which for a 25 gram mouse comes to 5.6 mg/kg. Higher dosages of up to 42 mg/kg could be reached by making a stock solution of compound 6 in DMSO further diluting it into saline for injection. At the highest injectable doses, mice injected with compounds 4 or 6 did not show any signs of toxicity. Mice injected with AMB at twice the $LD_{50}$ die instantaneously. This experiment shows that mouse $LD_{50}$ values of Compound 4 and 6 are at least 20-40 fold higher, respectively than AMB.

Example 6B: In Vivo Efficacy of PAD-AMB in Mice

Figure 5:
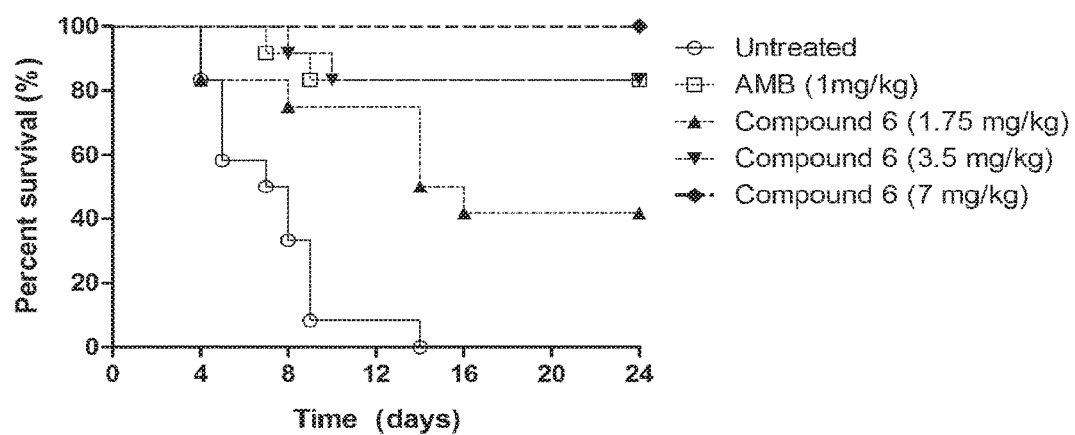
FIG. 5 shows a Kaplan-Meyer survival curve over 24 days showing survival of mice challenged with C. albicans and treated with various doses of AMB, compound 6 versus C. albicans challenged, untreated mice.

Reference is made to FIG. 5. Efficacy of PAD-AMB was tested on naïve 6 week old female ICR mice (n=20). Experimental systemic murine candidiasis was induced by intravenous inoculation of *C. albicans* CBS 562 into the tail vein using an inoculum of $5 \times 10^4$ cells in 0.2 ml per mouse. Fungal count was determined by microscopic counts on a haemocytometer. Treatment began 24 h after inoculation of *C. albicans* and consisted of four consecutive daily injections of Compound 6 at a range of 1.75-8.75 mg/kg/day relative to mouse body weight. Control groups included infected untreated mice and mice treated with AMB (1 mg/kg/day body weight). Survival and mouse body weight were monitored for 24 days. Survival for the various mouse groups is shown graphically in FIG. 5.

AMB at 1 mg/kg, which is nearly the maximal tolerated dose (MTD), rescued 10 of the 12 mice in the group. Compound 6 required a higher dose, 3.5 mg/kg to achieve the same level of efficacy. At 7 mg/kg, which is still far below the MTD, compound 6 rescued all of the mice from the fungal challenge.

Example 6C: Fungal Burden in Infected Mice Treated with PAD-AMB

Reference is made to FIGS. 6A-E. ICR female mice were inoculated with *C. albicans* in groups of 3 as described in example 6B and were killed 48 hours later for assessment of fungal burden. One kidney and the spleen were removed aseptically from each animal and homogenized in 1 mL of sterile normal saline. Serial 10-fold dilutions of the homogenates were spread on YAG plates, and colony-forming units (CFU)/organ was determined from the colony count after 24 hours incubation at 37° C. All mouse experiments were performed in duplicates.

At necropsy, fungal burden in mouse tissues was evaluated. Fontana-Masson silver staining of paraffin-embedded sections of kidneys from infected mice are shown in FIG. 6A-E. FIG. 6A shows a micrograph from kidney of infected, untreated mice. FIG. 6B shows a micrograph from kidney of AMB-treated mice. FIGS. 6C-E show micrographs of mice treated with Compound 6 at dosages of 1.75 mg/kg, 3.5 mg/kg and 7 mg/kg, respectively. As shown in FIG. 6A, fungal hyphae are abundant in the kidneys of untreated mice and barely detectable in mice treated with AMB or with PAD-AMB (FIGS. 6B-E).

Figure 7B:
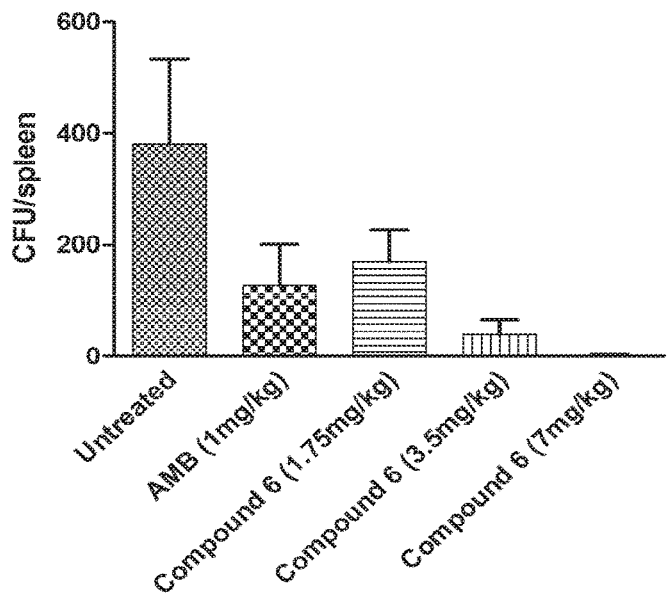

Fungal burden values in kidneys and spleens in terms of CFU per organ shown in FIGS. 7A and 7B are in agreement with the efficacy data presented in Example 6B.

Example 6D: Pharmacokinetics Upon Single Administration of PAD-AMB to Mice

AMB and Compound 6 solution in saline were administrated intravenously (IV) to groups of mice at a dose of 1 and 5 mg/kg body weight, respectively. The mice received an IV bolus via the tail vein. Mice were bled over a 48 h period at the following time points: 0, 5, 15 and 30 minutes and 1, 2, 6, 12, 24 and 48 h post-dosing (3 mice per time point). Bleeding was conducted using a facial vein technique into sterile Eppendorf tubes. Whole blood samples of 150 µl were collected at each time point, stored for 30 min at room temperature for clotting and centrifuged at 10,000 RPM for 10 minutes until serum separated. The serum samples were stored at −20° C.

The concentration of Compound 6 in the serum was measured by HPLC as follows: UltiMate® 3000 system (Dionex) was used equipped with 3000 pump, VWD-3000 UV-Vis detector and Chromeleon® 6.80 software. The column used was LiChroCART® 250×4.6 mm Purospher® STAR (5 µm) C-18 RP (reverse phase). Chromatographic conditions: flow: 1.0 ml/min, linear water (buffer A)/acetonitrile (ACN) (buffer B) gradient (buffer A—100% water, 0.1% TFA; buffer B—100% ACN, 0.1% TFA).

200 µl of methanol was added to 100 µl of serum sample and vortexed for 20 seconds, stored for 30 min at room temperature (22° C.), then centrifuged at 14,000 RPM for 10 minutes. The supernatant was filtered through a 0.22 µm filter and aliquots of 100 µl were analyzed by HPLC. AMB and Compound 6 were detected at a wavelength of 407 nm.

Figure 8A:
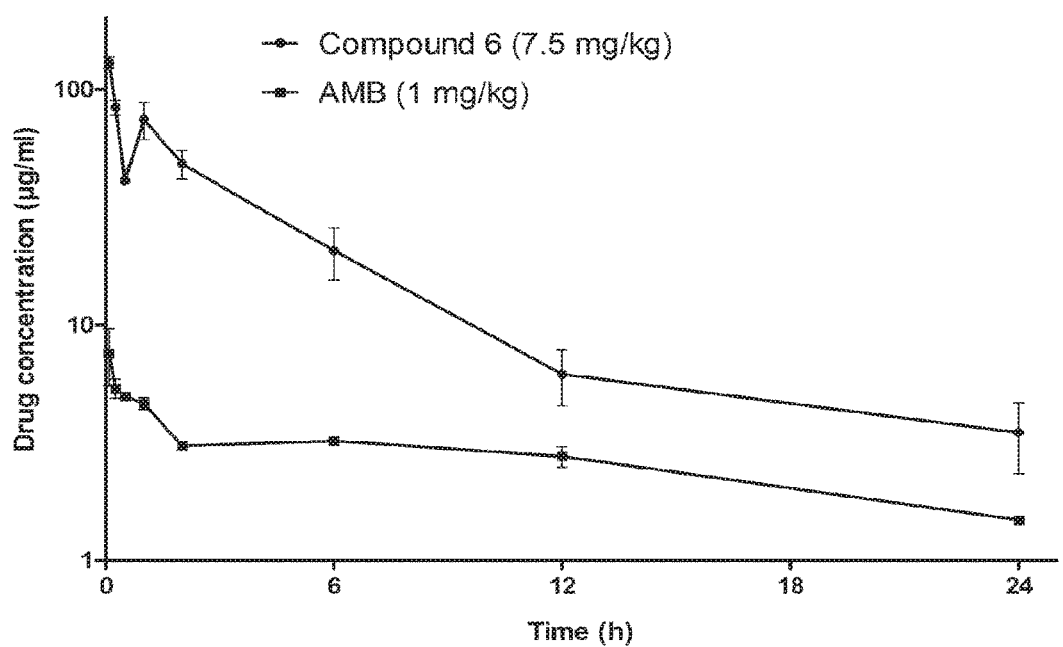
FIGS. 8A-B shows a graph of concentration in μg/ml of AMB and Compound 6 over a time period of 24 hours (8A) and over 120 minutes (8B) in mouse serum following a single intravenous administration.
Figure 8B:
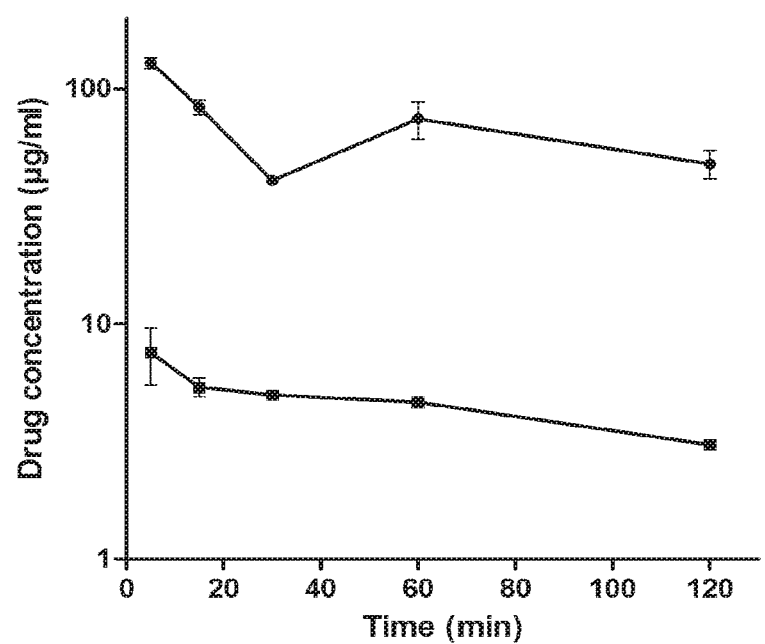

The pharmacokinetic graphs depicting drug concentration over time are shown in FIGS. 8A-8B (over 24 hours and 120 minutes respectively) and the calculated PK values are shown in Table 6 below.

TABLE 6

| Compound | $k_e$ (h) | $t_{1/2}$ (h) | $V_d$ (L) | CL (ml/h) | $AUC_{0-24}$ (µg*h/ml) | $MRT_{0-24}$ (h) |
|---|---|---|---|---|---|---|
| AMB | 0.043 | 15.964 | 0.006 | 0.250 | 63.983 | 9.664 |
| Compound 6 | 0.220 | 3.153 | 0.002 | 0.508 | 421.234 | 5.431 |

An interesting observation is that Compound 6 has a faster rate of elimination and a shorter serum half-life than AMB (15.96 h versus 3.153 h). This further supports the finding of stability shown in vitro in example 4b, indicating that the PAD-AMB relatively non-labile amide bond is not readily broken under physiological conditions, and that the PAD-AMB molecule is the active moiety and does not act as a prodrug as AMB derivatives with labile linkers do.

Discussion of Examples

The aforementioned examples show that PAD-AMB, in particular compounds 4 and 6, show increased solubility and much less toxicity than AMB. Although PAD-AMB levels required to show equivalent effect against certain fungal strains were higher than AMB, the decreased toxicity of the PAD-AMB make them viable candidates for use in antifungal and other clinical applications. Whereas native AMB administration is limited by its maximum tolerated dose of about 1 mg/kg body weight per day for a mouse, PAD-AMB showed significantly reduced toxicity profiles. This enables using larger doses of drug when necessary without reaching the acute toxicity limits. PAD-AMB molecules showed improved profiles: high stability in serum, increased solubility in aqueous media, reduced in vivo toxicity, high in vivo efficacy and an improved pharmacokinetic profile. All these properties significantly increase the therapeutic index of these compounds making them potential candidates for clinical use.

There is therefore provided, in accordance with embodiments of the invention, a PAD-AMB compound according to formula [I]:

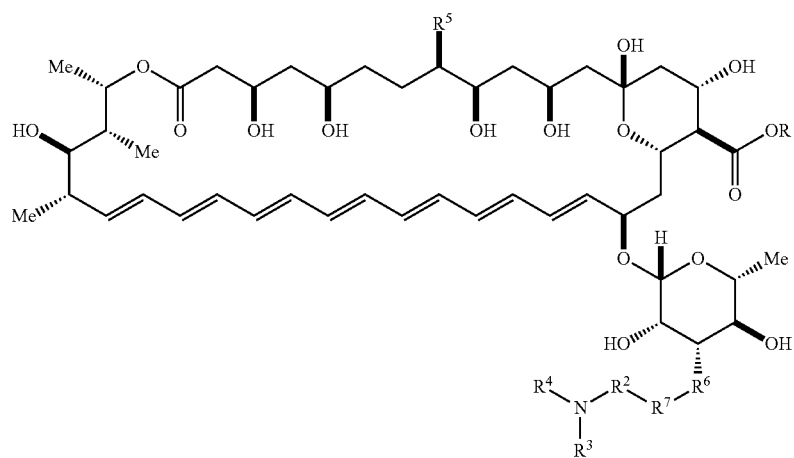

wherein R is H, $C_{1-4}$ alkyl or phenyl; $R^2$ is $(CH_2)_m$ wherein m is between 0 and 4; $R^3$ and $R^4$ are each independently H or $C_{1-4}$ alkyl, $R^5$ is H or OH, $R^6$ is selected from a group consisting of: amide and alkyl, and $R^7$ is a water-soluble polymer, and pharmaceutically acceptable salts, solvates, hydrates, diastereomers, and prodrugs of the compound of Formula [I].

In certain embodiments of the invention, the amide is selected from a group consisting of: organic amide, sulfonamide, sulfenyl amide and phosphoramide.

In certain embodiments of the invention, the water-soluble polymer is a PEG group consisting of p PEG monomers, wherein p is from 6 to 40. Optionally, p from 6 to 10. Optionally, p is 8.

In certain embodiments of the invention, the PAD-AMB compound is in accordance to formula [II]:

AMB according to an embodiment of the invention, including mixtures in all ratios, the process comprising: reacting Amphotericin B with a protected N-hydroxysuccinimide ester of PEG, and removing the protection. Optionally, the reaction is performed under one or more of the following conditions: the N-hydroxysuccinimide ester of PEG is protected by a FMOC group; reactants Amphotericin B and/or the protected N-hydroxysuccinimide ester of PEG are solutes in a non-aqueous solvent; the reaction is performed in the presence of a tertiary amine; the reaction is performed under an inert atmosphere; the reaction is performed in a light-free environment; a reaction mixture comprising Amphotericin B and the protected N-hydroxysuccinimide ester of PEG is stirred for at least an hour; and a reaction

[II]

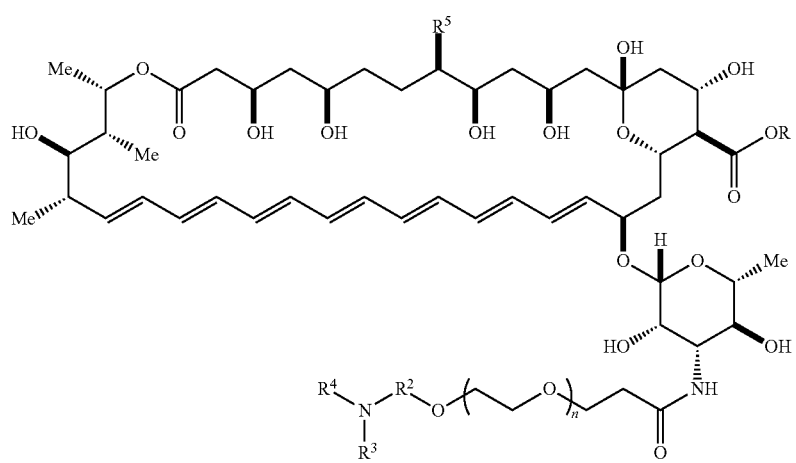

wherein R is H, $C_{1-4}$ alkyl or phenyl; $R^2$ is $(CH_2)_m$ wherein m is between 1 and 4; $R^3$ and $R^4$ are each independently H or $C_{1-4}$ alkyl, $R^5$ is H or OH, and n is between 5 and 39, and pharmaceutically acceptable salts, solvates, hydrates, diastereomers, and prodrugs of the compound of Formula [I].

Optionally, n is between 5 and 9.

Optionally, R is H, $R^2$ is ethyl; $R^3$ and $R^4$ are each H, $R^5$ is OH and n is 7.

Optionally, R is methyl, $R^2$ is ethyl; $R^3$ and $R^4$ are each H, $R^5$ is OH and n is 7.

There is also provided, in accordance with embodiments of the invention, a process for the preparation of the PADproduct is isolated from the reaction mixture, by passing the reaction mixture via a chromatographic column.

Optionally, the removal of the protecting group is by hydrolysis, optionally carried out in the presence of a weak base.

There is also provided, in accordance with certain embodiments of the invention, a pharmaceutical composition comprising: a PAD-AMB in accordance with an embodiment of the invention, including mixtures in all ratios; and a pharmaceutically acceptable carrier or diluent.

In certain embodiments of the invention, the PAD-AMB is according to formula [II]

[II]

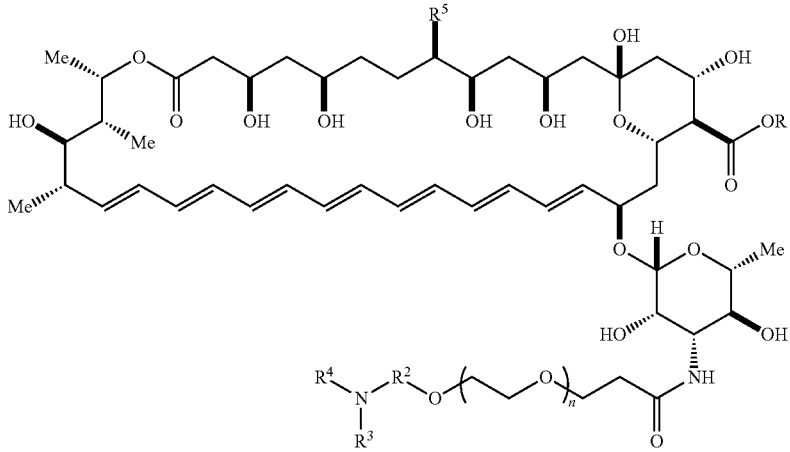

wherein R is H, $C_{1-4}$ alkyl or phenyl; $R^2$ is $(CH_2)_m$ wherein m is between 1 and 4; $R^3$ and $R^4$ are each independently H or $C_{1-4}$ alkyl, $R^5$ is H or OH, and n is between 5 and 39, and pharmaceutically acceptable salts, solvates, hydrates, and diastereomers thereof, including mixtures thereof in all ratios.

In certain embodiments of the invention, the diluent comprises at least 50% v/v water and the concentration of the at least one compound according to formula [II] is at least 0.01 mg/ml.

There is also provided, in accordance with certain embodiments of the invention, a method for the treatment of a disease comprising administering to a patient in need thereof, a therapeutically effective amount of a PAD-AMB in accordance with an embodiment of the invention, including mixtures in all rations.

In certain embodiments of the invention, the PAD-AMB is according to according to formula [II]

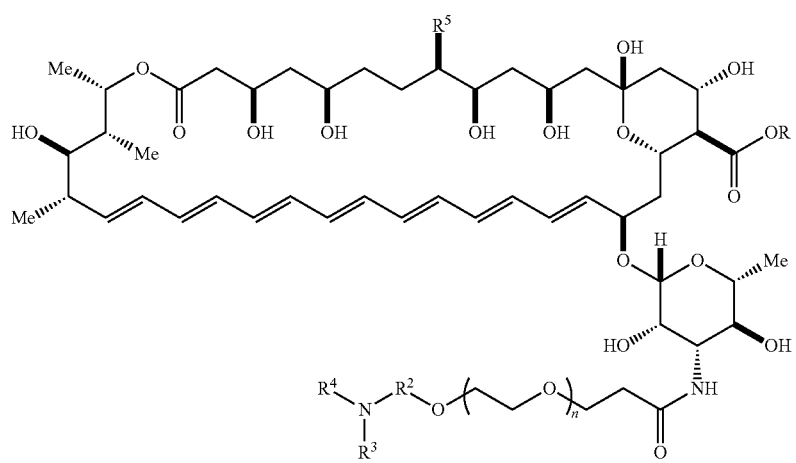

[II]

wherein R is H, $C_{1-4}$ alkyl or phenyl; $R^2$ is $(CH_2)_m$ wherein m is between 1 and 4; $R^3$ and $R^4$ are each independently H or $C_{1-4}$ alkyl, $R^5$ is H or OH, and n is between 5 and 39, and pharmaceutically acceptable salts, solvates, hydrates, and diastereomers thereof, including mixtures thereof in all ratios.

In certain embodiments of the invention, the disease is selected from the group consisting of: a fungal disease, a protozoan disease, a viral disease and a prion disease. Optionally, the disease is a fungal disease. Optionally, the fungal disease is of a fungus selected from the group consisting of one or two or more of: *Aspergillus, Candida, Cryptococcus* and *Pneumocystis*.

In certain embodiments of the invention, the compound of formula II is administered at a dosage of between 0.5 milligrams per kilogram bodyweight (mg/kg) and 10.0 mg/kg per day. Optionally, the daily dosage is between 0.5 mg/kg and 4.0 mg/kg daily.

In the description and claims of the present application, each of the verbs, "comprise," "include" and "have," and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A pharmaceutical composition comprising:
at least one compound according to Formula [I]

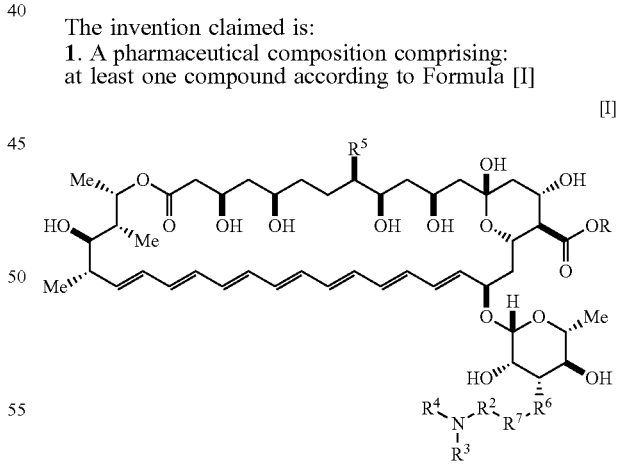

[I]

wherein R is H, $C_{1-4}$ alkyl or phenyl; $R^2$ is $(CH_2)_m$ wherein m is between 0 and 4; $R^3$ and $R^4$ are each independently H or $C_{1-4}$ alkyl, $R^5$ is H or OH, $R^6$ is selected from a group consisting of: amide and alkyl, and $R^7$ is a water-soluble PEG polymer having p PEG monomers, wherein p is from 6 to 40, or pharmaceutically acceptable salts, solvates, hydrates, and diastereomers thereof, including mixtures thereof in all ratios, and
a pharmaceutically acceptable carrier or diluent.

2. The pharmaceutical composition of claim 1, wherein the diluent comprises at least 50% v/v water and the concentration of the at least one compound according to Formula [I] is at least 0.01 mg/ml.

3. A method for the treatment of a disease, comprising administering to a patient in need thereof a therapeutically effective amount of a compound according to Formula [I]

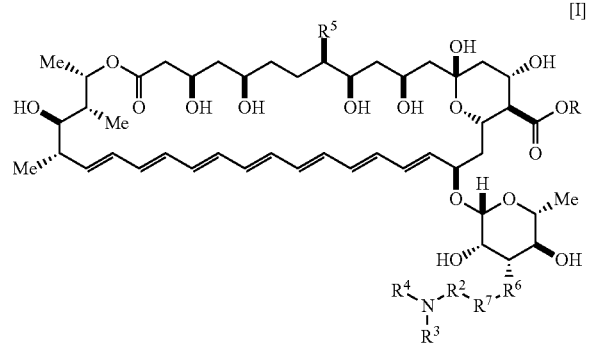

wherein R is H, $C_{1-4}$ alkyl or phenyl; $R^2$ is $(CH_2)_m$ wherein m is between 0 and 4; $R^3$ and $R^4$ are each independently H or $C_{1-4}$ alkyl, $R^5$ is H or OH, $R^6$ is selected from a group consisting of: amide and alkyl, and $R^7$ is a water-soluble PEG polymer having p PEG monomers, wherein p is from 6 to 40, or pharmaceutically acceptable salts, solvates, hydrates, and diastereomers thereof, including mixtures thereof in all ratios.

4. The method according to claim 3, wherein the disease is selected from the group consisting of: a fungal disease, a protozoan disease, a viral disease and a prion disease.

5. The method of claim 3, wherein the disease is a fungal disease.

6. The method of claim 5, wherein the fungal disease is of a fungus selected from the group consisting of *Aspergillus, Candida, Cryptococcus* and *Pneumocystis*.

7. The method of claim 3, wherein the compound of Formula I is administered at a dosage of between 0.5 milligrams per kilogram bodyweight (mg/kg) and 10.0 mg/kg per day.

8. The method of claim 7, wherein the daily dosage is between 0.5 mg/kg and 4.0 mg/kg daily.

9. The pharmaceutical composition according to claim 1, wherein the amide is selected from a group consisting of: organic amide, sulfonamide, sulfenyl amide and phosphoramide.

10. The pharmaceutical composition according to claim 1, wherein p is from 6 to 10.

11. The method of claim 3, wherein the disease is a protozoan disease.

12. The method of claim 11, wherein the protozoan disease is leishmaniasis.

* * * * *